United States Patent [19]
Jormanainen et al.

[11] Patent Number: 5,679,263
[45] Date of Patent: Oct. 21, 1997

[54] METHOD AND APPARATUS FOR PRODUCING FEED MIXTURE

[75] Inventors: Martti Johannes Jormanainen, Espoo; Launo Leo Lilja; Valto Johannes Mäkitalo, both of Pori, all of Finland

[73] Assignee: ECO Technology JVV OY, Espoo, Finland

[21] Appl. No.: 295,894

[22] PCT Filed: Mar. 16, 1993

[86] PCT No.: PCT/FI93/00094

§ 371 Date: Feb. 15, 1995

§ 102(e) Date: Feb. 15, 1995

[87] PCT Pub. No.: WO93/18847

PCT Pub. Date: Sep. 30, 1993

[30] Foreign Application Priority Data

Mar. 17, 1992 [FI] Finland .................... 921132

[51] Int. Cl.⁶ .................... B03B 5/30; B01D 12/00; B01D 37/00
[52] U.S. Cl. .................... 210/767; 210/787; 210/519; 210/532.1; 210/535; 210/540; 209/172.5; 209/173; 435/289.1
[58] Field of Search .................... 209/172, 172.5, 209/173; 210/520, 532.1, 534, 535, 540, 767, 787; 435/289.1

[56] References Cited

U.S. PATENT DOCUMENTS

| | | | |
|---|---|---|---|
| 2,799,396 | 7/1957 | Belaskas | 210/535 |
| 3,399,775 | 9/1968 | Ciaffone | 210/535 |
| 4,994,179 | 2/1991 | Keefer et al. | 210/534 |
| 5,061,375 | 10/1991 | Oyler | 210/534 |
| 5,405,530 | 4/1995 | Weiler et al. | 210/535 |

FOREIGN PATENT DOCUMENTS 8900151 1/1989 WIPO .................... C02F 11/04

Primary Examiner—David A. Redding
Attorney, Agent, or Firm—Brooks Haidt Haffner & Delahunty

[57] ABSTRACT

The invention relates to a method and apparatus for producing a feed mixture, advantageously suitable to an anaerobic bioreactor and containing liquid and solid materials, for the further treatment of waste materials. The method of the invention includes at least the following steps:

a) into a feed mixture reactor (1), there is first fed liquid so that the free liquid surface (5) is located essentially above the solid material feed point (6) provided in the reactor (1), b) the solid waste material fed into the feed mixture reactor (1) is fed to below the free liquid surface (5) of the reactor (1), and from the solid waste material there is separated (10, 14) both light and heavy rejectable materials by utilizing an agitator (7) installed in the feed mixture reactor (1), and countercurrent washing (14) directed towards the bottom part of the reactor (1). In the apparatus of the invention, the feed points (2, 17) of the liquid and sludgy waste materials to be fed into the feed mixture reactor are arranged on a lower level with respect to the agitator (7), and the feed point (6) of the solid waste material to be fed into the feed mixture reactor is arranged on a higher level than the agitator (7).

10 Claims, 2 Drawing Sheets

METHOD AND APPARATUS FOR PRODUCING FEED MIXTURE

BACKGROUND OF THE INVENTION

Field of the Invention

The present invention relates to a method and apparatus for producing a feed mixture suitable to an anaerobic bioreactor.

While the importance of environmental issues, with respect to people's welfare, increases daily, the created waste must be treated so that it causes as little damage as possible, or that it can be reused. The anaerobic bioreactor is a generally known waste treatment unit for solid organic waste, such as organic matter sorted out from ordinary municipal waste. However, an advantageous operation of the anaerobic bioreactor requires that the material treated in the reactor undergoes a suitable preliminary treatment prior to feeding.

The object of the present invention is to eliminate some of the drawbacks of the prior art and to create an improved method and apparatus for producing a feed mixture which is suitable to be fed for instance to an anaerobic bioreactor. The essential novel features of the invention are apparent from the appended patent claims.

SUMMARY OF THE INVENTION

According to the invention, solid organic waste undergoes a preliminary treatment where the waste is turned into a feed mixture for an anaerobic bioreactor, which feed mixture has various predetermined qualities. Among these qualities, let us point out a suitable solid matter content defined by biological operation, technical applicability and economical profitability. Another requirement for the feed mixture is that the temperature of the mixture is advantageous for the functions of bacteria. Moreover, in order to improve flowing and mixing properties, heavy inorganic particles surpassing a predetermined grain size, for example stone, glass and metal, as well as light particles which easily rise to the surface of the feed mixture, such as plastic and cork, are separated from the mixture before feeding it into an anaerobic bioreactor.

The apparatus of the invention, i.e. the feed mixture reactor used for producing the said feed mixture, is advantageously for instance a cylindrical tank operated in an essentially vertical position, which tank is provided for example with essentially conical members, so that inside the feed mixture reactor, advantageous conditions are created for the material contained therein, for instance with respect to the flowing of the material, in order to create the desired feed mixture. Inside the feed mixture reactor, there is installed an agitating member for preparing an advantageously homogeneous feed mixture. The feed mixture reactor is also provided with conduits for feeding waste materials and liquids used in the feed mixture, as well as for removing ready-made feed mixture to be conducted to further treatment, for instance to a bioreactor. Moreover, there are specific conduits for discharging heavy and light particles to be separated from the waste.

In the method of the invention, into the feed mixture reactor there is first fed preheated liquid, so that the feed point of the solid waste supply conduit inside the feed mixture reactor is located underneath the liquid surface. The liquid fed into the feed mixture reactor can advantageously be water, but some other liquid matter, containing for instance components that are advantageous for the bioreactor process, can also be used. The liquid is fed into the feed mixture reactor through conduits installed advantageously to the bottom part of the reactor, on an essentially lower level than the agitating member. After supplying the liquid, solid waste is fed into the reactor so that the surface formed by the mixture of the feed material and liquid reaches the desired height level. The light particles contained on the surface of the mixture are removed as overflow, and when necessary, a scraping device provided in the feed mixture reactor is used. The heavy particles obtained along with the waste are discharged at the bottom part of the reactor, advantageously through an outlet conduit provided at the end of the conical member. In the removal of heavy particles, there is employed countercurrent washing, so that only those particles that surpass the desired limit, such as 10 mm, are let out of the feed mixture reactor.

The waste material to be fed into the feed mixture reactor of the invention can also be composed of both solid and sludgy materials, in cases where it is desired to treat both solid and sludgy waste materials in one and the same bioreactor. In order to render the feed mixture reactor hygienic and odorless, the sludgy material is advantageously fed only after removing the rejected light and heavy particles. Advantageously the sludgy material is sludge from a waste treatment plant, for instance from a municipal sewage treatment plant.

The solid content of the solid waste material to be fed into the feed mixture reactor of the invention is 30–50%, advantageously 45–50%. In connection with feeding sludge from a waste treatment plant or, in case sludge is not fed, already in connection with feeding solid waste material, the solid content is adjusted to the final level which advantageously is 10–15% of the weight of the whole mass contained in the feed mixture reactor. Depending on the reaction balance of the bioreactor successive to the feed mixture reactor, the temperature of the feed mixture is adjusted either within the range 35°–38° C., when the bioreactor is operated in the mesophile area, or within the range 55°–60° C., when the bioreactor is operated in the thermophile area.

The invention is described in more detail below, with reference to the appended drawings, where

DETAILED DESCRIPTION OF PREFERRED EMBODIMENTS

Figure 1:
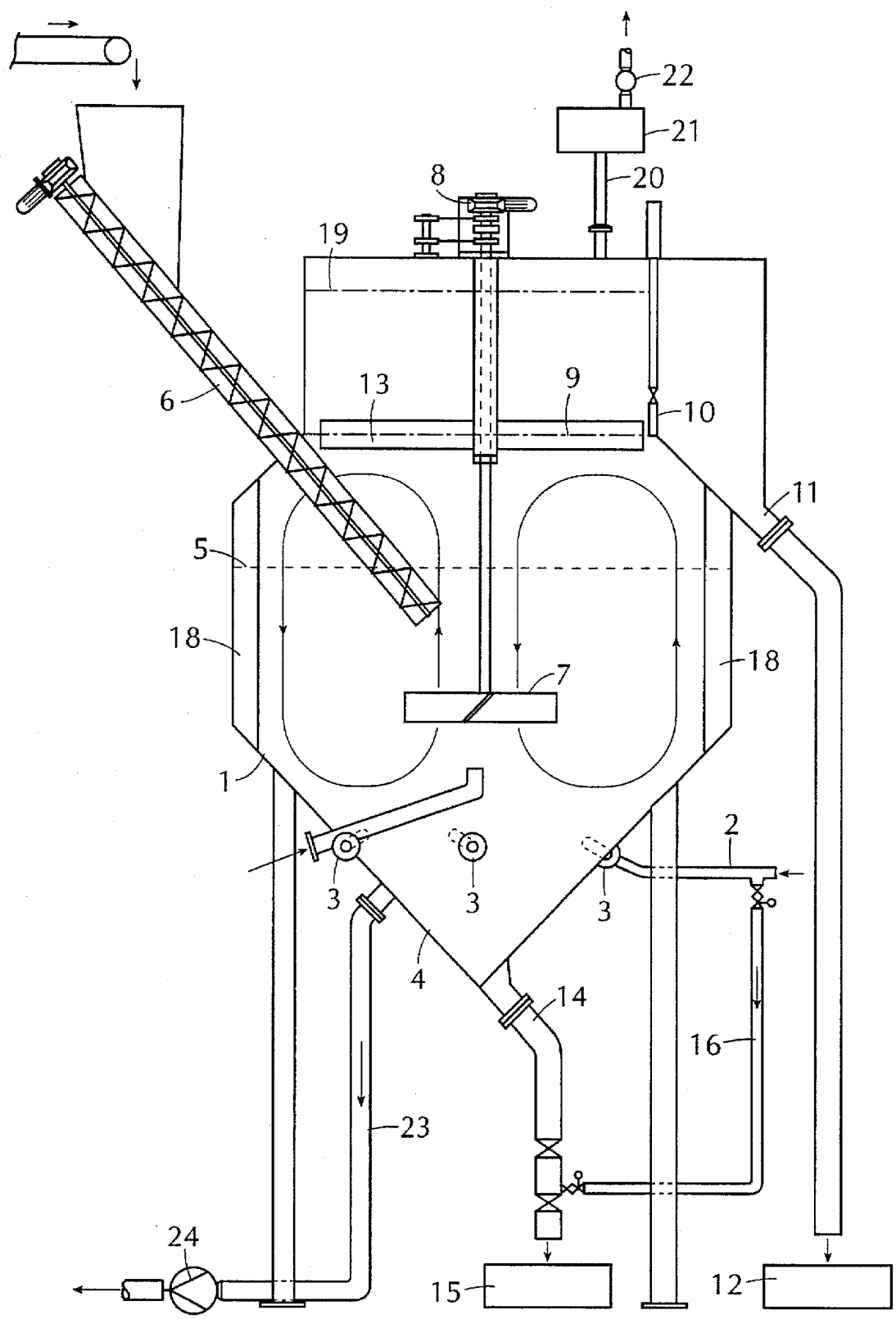
FIG. 1 illustrates a preferred embodiment of the invention, seen from the side.

In the embodiment of FIG. 1, the production of the feed mixture is started so that into an empty feed mixture reactor 1, there is conducted preheated water through the conduit 2. The water entering from the conduit 2 is directed into the reactor 1 radially upwards, by means of nozzles 3, so that at the same time any remains of the previous feed mixture batch, possibly stuck onto the bottom cone surface 4, are washed off. Water is fed into the reactor 1 so long that it reaches the level 5.

The solid waste material is fed into the reactor 1 through the feed apparatus 6. The end of the feed apparatus 6 is advantageously underneath the top level 5 of the water surface, so that the feed point of the waste material is advantageously located in a rising current. The rising current is created by means of an agitator 7 rotated by a motor 8.

Thus the solid waste material is spread due to the agitation flow and distributed preferably symmetrically along the whole transversal surface of the reactor 1. The feeding of solid waste material is stopped when the surface of the mixture of water and waste reaches the level 9.

During the feeding of solid material into the feed mixture reactor of the invention, the agitation speed and direction of the agitator 7 are advantageously chosen so that particles smaller than the desired grain size and distinctly heavier than water move along with the agitation flow, and particles larger than the desired grain size settle down on the reactor bottom for removal. The rejectable material that rises onto the surface of the water-and-solid mixture is discharged from the reactor through the discharge hatch 10 located essentially on the level 9. The shifting of the rejected material, to be let out from the discharge hatch 10, to the outlet channel 11 and further to the discharge tank 12 can, when necessary, be intensified by means of a surface scraper 13 connected to the discharge hatch 10.

During the agitation of the solid-and-water mixture in the feed mixture reactor, the heavy rejectable material settled on the bottom of the reactor 1 is removed from the reactor via the conduit 14 to the discharge tank 15. This heavy rejectable material is advantageously flushed in a countercurrent wash by conducting washing water to the conduit 14 via the conduit 16. The grain size of the separated heavy rejectable material is adjusted to be suitable by adjusting the strength of the countercurrent wash.

After removing light and heavy rejectable materials, both the light waste discharge hatch 10 and the heavy waste discharge hatch 14 are closed, and agitation is continued with the agitator 7, until the feed mixture prepared in the feed mixture reactor essentially corresponds to the solid matter content and temperature values desired in the next bioreactor.

Figure 2:
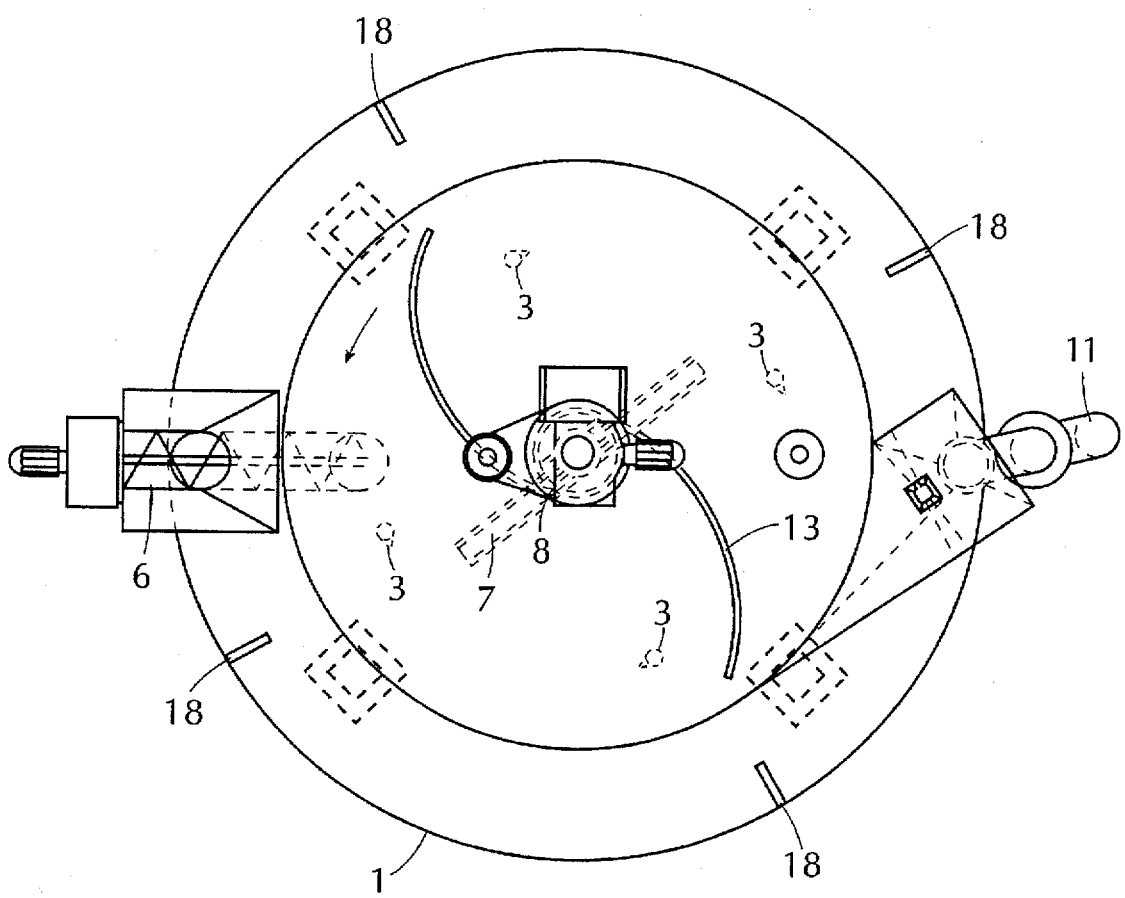
FIG. 2 illustrates the embodiment of FIG. 1, seen from the top.

If some organic waste treatment sludge, such as predried sewage sludge, is fed into the feed mixture reactor of the invention in addition to water and solid waste, both the light waste discharge hatch 10 and the heavy waste discharge hatch 14 are closed prior to feeding this additional sludge. Thus the waste treatment sludge can be fed into the feed mixture reactor only after the removal of light and heavy rejectable materials, in which case both the process and the rejectable materials can be rendered essentially more odorless and hygienic. The waste treatment sludge is fed into the feed mixture reactor of the invention through the feed conduit 17. Preferably the feed conduit 17 is installed essentially on the same vertical axis with the axis of the agitator 7, so that the feed point of the waste treatment sludge is advantageous with respect to the rising current created by the agitator 7. In order to improve the evenness of the rising current, the wall of the feed mixture reactor 1 is provided with radially arranged flow baffles 18, as is illustrated in FIG. 2. Thus an essentially rapid agitation and essentially symmetrical load is achieved in the feed mixture reactor.

The feeding of waste treatment sludge is stopped, when the surface of the feed mixture advantageously reaches the level 19. At least during the feeding of waste treatment sludge, the exhaust gases from the feed mixture reactor 1 are conducted, via the outlet conduit 20, advantageously for instance to a biofilter 21. By means of a blower 22 connected to the outlet conduit 20, the whole feed mixture reactor 1 can, when necessary, be kept in underpressure, so that for instance odor nuisances connected to waste treatment can essentially be avoided. After feeding waste treatment sludge, the agitation of the feed mixture is continued with the agitator 7, until the feed mixture is essentially homogeneous and its solid content and temperature are advantageous with respect to the next bioreactor process. The ready-made feed mixture is pumped, via the outlet conduit 23, to the next process stage by the pump 24.

We claim:

1. A method for producing a feed mixture, advantageously suitable to an anaerobic biorector and containing liquid and solid materials, for the further treatment of waste materials comprising at least the following steps:

a) into a feed mixture reactor, there is first fed liquid so that a free liquid surface is located essentially above a solid material feed point provided in the reactor, b) the solid waste material fed into the feed mixture reactor is fed to below the free liquid surface of the reactor, and from the solid waste material there is separated both light and heavy rejectable materials by utilizing an agitator installed in the feed mixture reactor, and by countercurrent washing directed towards the bottom part of the reactor, wherein the waste material fed into the feed mixture reactor contains both solid waste material and sludgy waste material to be fed in after the removal of rejected materials.

2. A method according to claim 1, wherein the sludgy waste material to be fed into the feed mixture reactor is municipal sewage sludge.

3. A method according to any of the claims 1 or 2, wherein the solid material fed into the feed mixture reactor is solid municipal waste with a solid content of 30–50%.

4. A method according to any of the claims 1 or 2, wherein heavy particles are separated by means of countercurrent washing.

5. A method according to any of the claims 1 or 2, wherein at least during the feeding of sludgy waste material, the feed mixture reactor is kept in underpressure.

6. An apparatus for realizing the method of claim 1, provided with conduits for feeding liquid and conduits for feeding solid and sludgy waste materials, means for agitating the material contained in the reactor, conduits for removing rejectable materials and conduits for discharging the feed mixture, wherein the feed points of the liquid and sludgy waste materials to be fed into the feed mixture reactor are arranged on a lower level with respect to the agitator and the feed point of the solid waste material to be fed into the feed mixture reactor is arranged on a higher level than the agitator.

7. An apparatus according to claim 6, wherein the liquid to be fed into the feed mixture reactor is fed through at least one nozzle connected to the wall of the reactor.

8. An apparatus according to claim 6 or 7, wherein the feed point of the sludgy waste material to be fed into the feed mixture reactor is located essentially on the same vertical axis as the axis of the agitator.

9. An apparatus according to any of the claims 6 or 7, wherein in order to improve the flowing, flow baffles are arranged radially on the wall of the feed mixture reactor.

10. A method according to claim 1, or 2, wherein the solid waste material fed into the feed mixture reactor is solid municipal waste with a solid content of 45–50%.

* * * * *

UNITED STATES PATENT AND TRADEMARK OFFICE
CERTIFICATE OF CORRECTION

PATENT NO. : 5,679,263
DATED : October 21, 1997
INVENTOR(S) : MARTTI JOHANNES JORMANAINEN ET AL.

It is certified that error appears in the above-identified patent and that said Letters Patent is hereby corrected as shown below:

Column 4, line 11, change "biorector" to --bioreactor--.

Signed and Sealed this

Twenty-third Day of December, 1997

Attest:

Attesting Officer

BRUCE LEHMAN

Commissioner of Patents and Trademarks